United States Patent
Monterenzi

(10) Patent No.: US 9,629,968 B2
(45) Date of Patent: Apr. 25, 2017

(54) DEVICE FOR SUPPLYING MICRONIZED MEDICAL SALT

(75) Inventor: Roberto Monterenzi, Prevalle (IT)

(73) Assignee: TECNO SUN S.R.L., Bedizzole (IT)

( * ) Notice: Subject to any disclaimer, the term of this patent is extended or adjusted under 35 U.S.C. 154(b) by 399 days.

(21) Appl. No.: 13/813,191

(22) PCT Filed: Jul. 29, 2011

(86) PCT No.: PCT/IB2011/053381
§ 371 (c)(1),
(2), (4) Date: Jan. 30, 2013

(87) PCT Pub. No.: WO2012/017365
PCT Pub. Date: Feb. 9, 2012

(65) Prior Publication Data
US 2013/0125888 A1   May 23, 2013

(30) Foreign Application Priority Data
Aug. 2, 2010 (IT) ............... BS2010A0136

(51) Int. Cl.
*A61M 15/00*   (2006.01)
*A61M 16/00*   (2006.01)
*A61M 15/02*   (2006.01)

(52) U.S. Cl.
CPC ......... *A61M 15/00* (2013.01); *A61M 15/0005* (2014.02); *A61M 15/0065* (2013.01); *A61M 15/02* (2013.01); *A61M 16/0066* (2013.01); *A61M 2202/066* (2013.01)

(58) Field of Classification Search
CPC ............... A61M 15/0028; A61M 15/0065; A61M 15/0033; A61M 15/0091; A61M 11/002; A61M 15/0025; A61M 15/0068; A61M 11/02; A61M 15/02; A61M 15/00; A61M 16/00; A61M 16/10; A61M 16/16; A61M 11/04; G01F 11/24; A61G 10/02; A47J 19/02; A47J 42/32; F23K 3/14; B29C 47/585; B29C 47/6037; B29C 47/6093; B29C 47/76; E21B 21/07; E21B 21/062; B65G 53/60; B65G 65/46; G03G 15/0877; G03G 15/0893
USPC ............ 128/200.24, 203.12, 203.15, 203.19, 128/203.21, 204.18, 204.21; 222/636
See application file for complete search history.

(56) References Cited

U.S. PATENT DOCUMENTS

| | | | |
|---|---|---|---|
| 4,007,675 A | | 2/1977 | Cailliot et al. |
| 4,046,146 A | * | 9/1977 | Rosskamp et al. ...... 128/203.15 |
| 4,328,913 A | * | 5/1982 | Whiteman ..................... 222/413 |
| 5,288,028 A | * | 2/1994 | Spivak et al. ................ 239/683 |
| 2005/0267628 A1 | | 12/2005 | Crowder et al. |

FOREIGN PATENT DOCUMENTS

| | | |
|---|---|---|
| WO | 2007054604 A1 | 5/2007 |
| WO | 2008084269 A2 | 7/2008 |

* cited by examiner

*Primary Examiner* — Annette Dixon
(74) *Attorney, Agent, or Firm* — Pearne & Gordon LLP

(57) ABSTRACT

The device (1) for supplying micronized medical salt comprises a container (2) for medical salt, having a vertical longitudinal development and a lower end portion (3) provided with a mouth of release (4) of the medical salt, a screw (20) inserted into the container and having an upper end (21) and a lower end (22) which is free, rotation members (30) of the screw mechanically connected thereto for rotating it with respect to the container, where the screw advances the medical salt downward so that the medical salt is released in a controlled manner from the mouth of release (4), the device further comprising a dispenser (50) which comprises a supply duct (51) and a ventilation member (60) which generates an air flow within the supply duct, where the mouth of release is in communication with the supply duct so as to release the medical salt directly in the air flow.

8 Claims, 3 Drawing Sheets

DEVICE FOR SUPPLYING MICRONIZED MEDICAL SALT

FIELD OF THE INVENTION

The present invention relates to a device for supplying micronized medical salt, e.g. for halotherapy treatments. Furthermore, the invention relates to a method for supplying a mixture of micronized medical salt by means of such a device.

DESCRIPTION OF RELATED ART

The halotherapy is a natural therapy which consists in administering, inhaled, medical sodium chloride, micronized and distributed within a confined environment, indicated for its therapeutic effects, for example in the treatment of bronchopulmonary pathology and skin pathology. The term "medical micronized salt" refers to sodium chloride suitable for use in medical therapies and finely pulverized into particles having dimensions, for example, between 1 and 100 micrometers.

Halotherapy typically involves the use of a mixture of salts having different granulometry between them, where granulometry means the dimensional property (e.g. the average diameter) of the particles (grains) of medical salt produced by a process of grinding.

It is known about devices capable to micronized, and then supply, a quantity of medical salt. These devices typically comprise a feeding container in which the medical salt to be micronized is introduced, a micronizer (e.g. a propeller or a pair of rollers) which grinds finely, typically mechanically and continuously, the medical salt contained in the container and supplies it in an environment in which is intended to realize an halotherapy treatment.

The Applicant has found that current devices for supplying micronized medical salt are not without drawbacks and can be improved under various aspects.

In particular, the Applicant has found that known devices are not capable to deliver a mixture of micronized medical salt having a predetermined granulometric composition. For example, entering a mixture of salts having predetermined granulometric composition (i.e. the distribution of the percentage fractions of the different granulometries), known devices change the granulometric composition due to the grinding by the micronizer.

A further drawback of known devices found by the Applicant consists in the adding to the medical salt, during the micronization and/or the distribution of the same, of unwanted substances such as, for example, external particles, plastic, metal, paint, which are released into the environment in which the device operates with the micronized medical salt.

A further drawback found by the Applicant consists in the impossibility, or extreme difficulty, of known devices to dose with sufficient accuracy the supplied medical salt and/or to vary such a dosage.

The Applicant also noted how known devices are plagued by a disadvantageous phenomenon of compaction of the medical salt inside the feeding container. This phenomenon is due to the small size of the particles of medical salt, which come together resulting in a possible clogging of the device and/or in a difficult supplying and/or the inability to supply medical salt having small dimensions.

An additional drawback of known devices resides in the industriousness of the loading of medical salt to be micronized into the feeding container.

The Applicant also found how known devices are characterized by a complex structure and/or by a high cost of implementation.

Under these circumstances, the aim underlying the present invention in its various aspects and/or embodiments is to provide a device for supplying micronized medical salt, which is able to obviate one or more of the drawbacks mentioned above.

BRIEF SUMMARY OF THE INVENTION

This aim and others, if any, that will be more apparent in the following description are substantially achieved by a device, and a relative method, for supplying micronized medical salt according to one or more of the appended claims, each of them being considered alone (without its related dependent claims) or in any combination with other claims, and according to the following aspects and/or embodiments, variously combined, also with the aforesaid claims. In one aspect, the invention relates to a device for supplying micronized medical salt comprising:

a container having a vertical longitudinal development and a lower end portion of cylindrical shape and provided with a mouth of release of the medical salt, the container being configured for containing a quantity of medical salt;

a screw inserted into said container and having an upper end and a lower end which is free in correspondence of said lower end portion;

rotation members of the screw mechanically connected to the upper end of the screw for rotating the latter with respect to the container, the screw being configured for advancing said medical salt downward along said longitudinal development through said rotation, so that the medical salt is released in a controlled manner from said mouth of release of the lower end portion and supported by the screw in any other point on the lower end portion of the container, the device further comprising a dispenser comprising a supply duct and a ventilation member for generating an air flow within the supply duct, where said mouth of release of the medical salt is in communication with the supply duct so as to release said medical salt directly in the aforesaid air flow and where the supply duct is configured so that said air flow is substantially horizontal at least in correspondence of said mouth of release.

The Applicant thinks that the combination of the aforesaid technical features, in particular the presence of the screw which permits to release the medical salt in a controlled manner from the mouth of release and to support it in any other point on the lower end portion of the container, and the fact that the mouth of release of the medical salt is in communication with the supply duct so as to release the medical salt directly into a horizontal air flow, allows to supply the micronized salt, contained in the container, into the treatment environment without subjecting it to any further step, such as for example a further step of micronization. In other words, the medical salt is supplied from the above, through the screw, with a controlled dosage and directly from the container in a horizontal air flow, which is apt to transport the medical salt from the supply duct toward the outside of the device, and to release it into the treatment environment. Moreover, the Applicant has verified that, for example due to the fact that the device supplies medical salt without using a micronizer, the micronized medical salt introduced into the container retains its physical characteristics, for example the granulometric composition, until the supplying from the supply duct.

In this context, the device object of this invention is configured for supplying a quantity of medical salt, already micronized, having specific characteristics and intended, when evenly diffused in an environment, to realize a specific halotherapy treatment.

The Applicant also believes that the aforesaid technical features, in particular the presence of the rotation members of the screw for rotating the latter with respect to the container, and the fact that the screw advances the medical salt downward through said rotation so that the medical salt is released in a controlled manner from the mouth of release of the lower end portion, allow to have a device with a high versatility and capable to dose with sufficient precision the supplied medical salt and/or to change such a dosage (e.g. the mass concentration).

In one aspect, the container has an upper portion of substantially truncated conical shape developing from an upper opening, from which the medical salt is introduced in the container, to the aforesaid lower end portion, said upper opening having a diameter greater than the diameter of said lower end portion.

In one aspect, the screw comprises a first screw, having a first pitch and developing entirely within said upper portion of the container, and a second screw, having a second pitch and developing lower than said first screw and until said lower end portion of the screw, said first and second screw being configured for rotating integrally with said screw and said first pitch being greater than said second pitch.

Preferably the second screw develops partially also within said upper portion of the container. In one aspect, said first screw has a truncated conical development substantially corresponding to the truncated conical shape of the upper portion of the container, so that the diameter of each portion of the first screw is substantially equal to the diameter of the corresponding section of the upper portion of the container. Thus the first screw, having a high diameter and pitch, keeps in movement a high amount of medical salt which is in the top part of the container allowing advantageously to avoid the compaction and the blocking of the medical salt in the container. The advance of the salt downward, as well as by the vertical orientation of the container, can be supported by the taper of the upper portion of the container, which facilitates the flow of the salt along the inner surface of the container.

In one aspect, said second screw, at least for the portion developing in correspondence of the lower end portion (preferably for its whole development), has a diameter which is constant and substantially equal to the diameter of the cylindrical lower end portion of the container. Thus the second screw, having a diameter and a pitch low and constant, allows to evenly advance the medical salt in the lower end portion toward the mouth of release of the salt, and to dose it accurately. Totally the screw, being provided with two screws, allows an efficient and controlled advance and dosage of the medical salt.

In one aspect, said first and/or second screw are medical salt tight with the inner walls of said upper portion and said lower end portion, respectively, of the container. Thus the screw advances the medical salt and simultaneously supports it inside the container, avoiding the leakage of medical salt between the screw and the inner walls of the container and, for example, the consequent lower exit, without intention, of the medical salt from the mouth of release or the escape from the first screw going to compact on the second screw. Thus, only the advance of the screw allows to lead the medical salt to the mouth of release, so the supply is controlled. In one aspect, rotation members comprise a motor provided with a mounting portion superiorly mounted to said container and with a driving shaft mechanically connected to, and integral with, the upper end of the screw.

In one aspect, the device comprises vibration members, stiffly fixed to said container and configured for vibrating said container. Thus it is possible to vibrate the medical salt in the container and prevent its compaction (typical for mixtures of medical salts finely micronized) inside the container, facilitating the advancement, by the screw, toward the mouth of release of the salt.

In one aspect, the device comprises at least a vibration damping system interposed between said container and said rotation members. Thus it is possible to decouple vibration members from rotation members, avoiding that the vibrations generated by the vibration members is transmitted to the rotation members, for which the vibrations are extremely harmful (especially if repeated over a long period of time) since they can create failures and breakages, for example of the engine components.

In one aspect, the present invention relates to a method for supplying micronized medical salt comprising the steps of introducing a mixture of micronized medical salt in the container of a device according to one or more of the aspects and/or claims; advancing said mixture in a controlled manner downward along the vertical longitudinal development of the container, by rotating the screw; releasing the mixture from the mouth of release of the lower end portion of the container within the supply duct; generating, by means of the ventilation member, an air flow inside the supply duct, the air flow being substantially horizontal at least in correspondence of the mouth of release; supplying the mixture, released into the air flow, from the supply duct.

In one aspect, in the step of introducing a mixture of micronized medical salt in the container, said mixture is drawn from an envelope containing a mixture of salts having the same chemical composition and different granulometry according to predetermined mass fractions. Thus it is possible to obtain a supply of a mixture of micronized medical salt having a predetermined granulometric composition and a certain dosage. Furthermore, it is possible to avoid the introduction of contaminants in the mixture of medical salt. The medical salt used in this invention is typical micronized medical salt previously prepared in controlled environments (e.g. having the correct humidity and free of dust and contaminants) and packaged in the envelope. Thus, by introducing into the envelope a given dose of a particular mixture of micronized medical salt (with predetermined features), it is possible to provide different cycles of halotherapy.

In one aspect, in the step wherein said mixture is drawn from an envelope, said envelope contains a mass percentage of micronized medical salt having a granulometry lower than 20 micrometers, preferably 15, and greater than 5 micrometers, preferably 10, between 5% and 10%, a mass percentage of micronized medical salt having a granulometry lower than 5 micrometers, preferably 3, between 1% and 5% and a mass percentage of micronized medical salt having a granulometry greater than 50 micrometers, preferably 100, between 85% and 94%. The Applicant, to its knowledge for the first time, has found in fact, through the execution of tests, how the addition into the mixture of finely micronized (e.g. less than 20 micrometers) medical salt of an amount approximately 10 times more of salt having a sufficiently large granulometry (e.g. greater than 100 micrometers) allows to keep dry and separate the finest particles, which otherwise would tend to compact together and/or to absorb moisture easily. Thus, it is possible to keep the mixture disaggregated and to promote an efficient operation of the device. It should be noted that keeping separate the finest particles is an objective of primary importance since these particles are responsible for more beneficial effects in a halotherapy treatment.

In one aspect the present invention relates to an assembly comprising a device according to one or more of the aspects and/or claims and the aforesaid envelope.

In one aspect, the assembly comprises the device according to one or more of the aspects and/or claims and a set of envelopes each containing a respective mixture of salts having the same chemical composition and different granulometry according to predetermined mass fractions. Further characteristics and advantages will be more evident from the detailed description of some exemplary though not exclusive embodiments, among which also a preferred embodiment, of a device for supplying micronized medical salt according to the present invention.

BRIEF DESCRIPTION OF THE DRAWINGS

This description will be disclosed below with reference to the accompanying drawings, provided to a merely indicative and therefore non-limiting purpose, in which.

DETAILED DESCRIPTION OF THE PREFERRED EMBODIMENTS OF THE INVENTION

Figure 1:
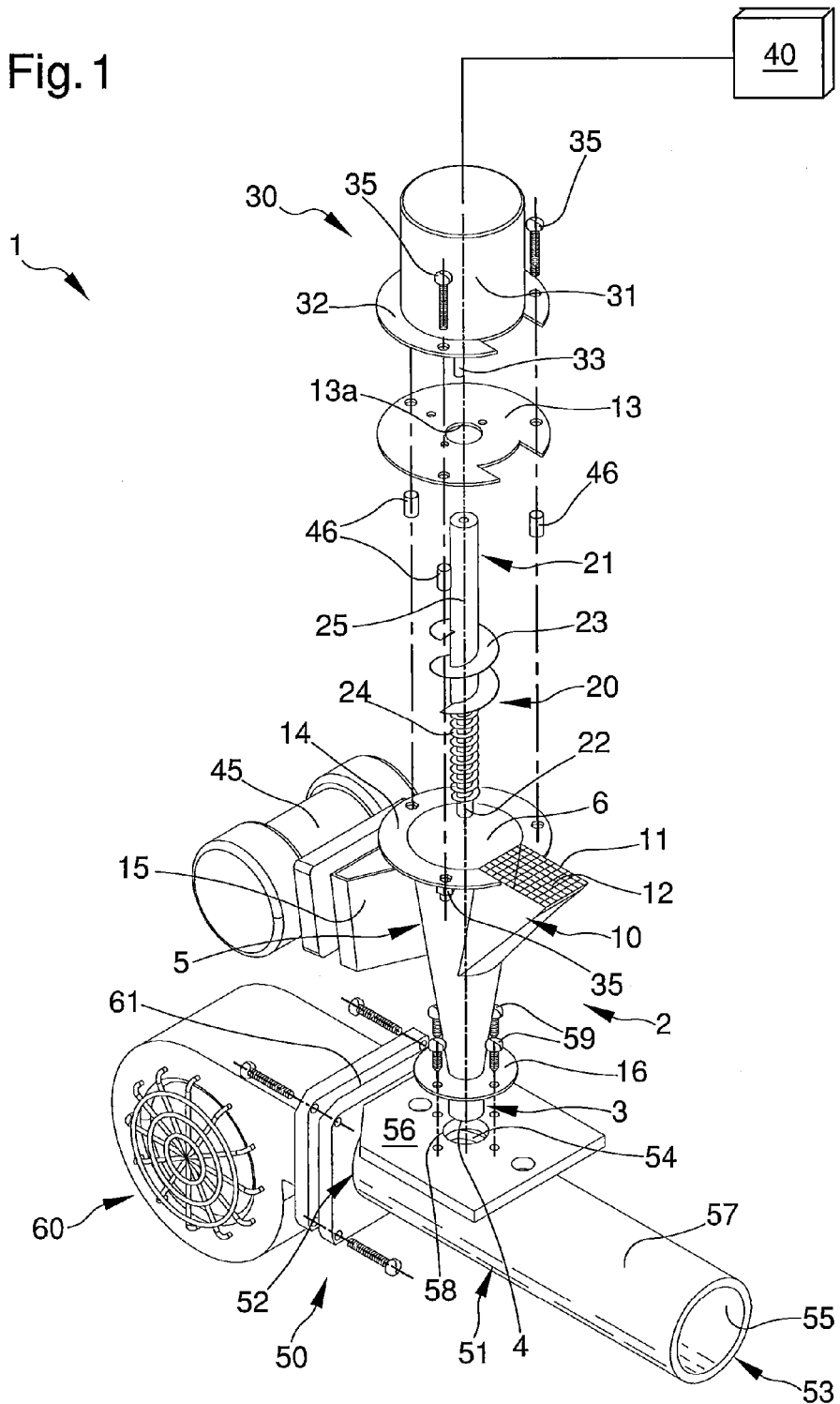
FIG. 1 is a perspective exploded view of a device for supplying micronized medical salt according to the present invention.
Figure 2:
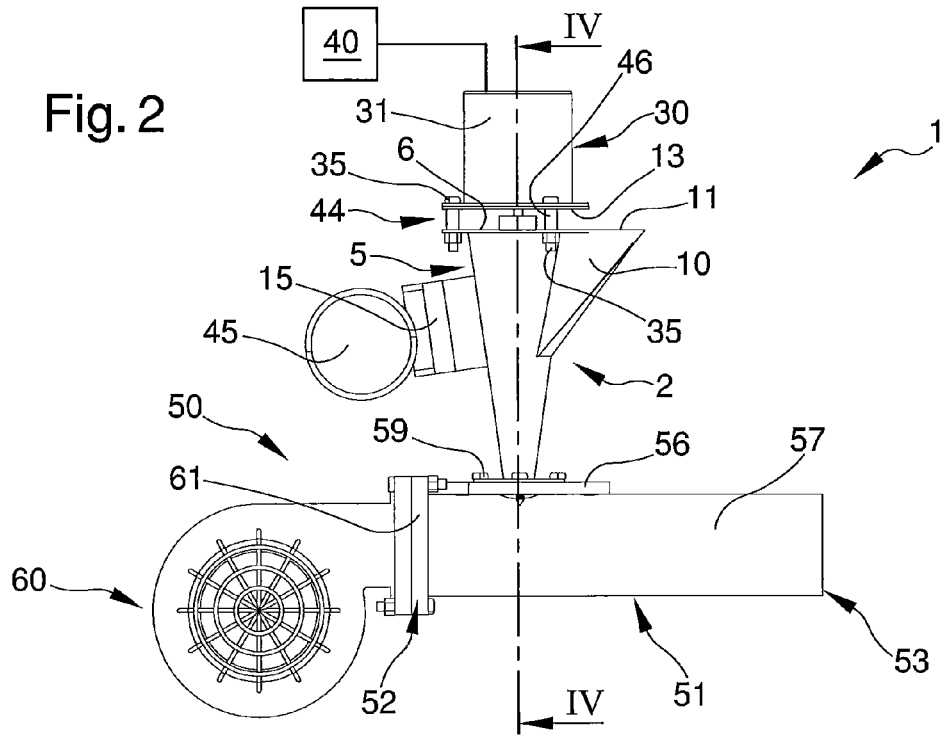
FIG. 2 is a side view of the device of FIG. 1 assembled.
Figure 3:
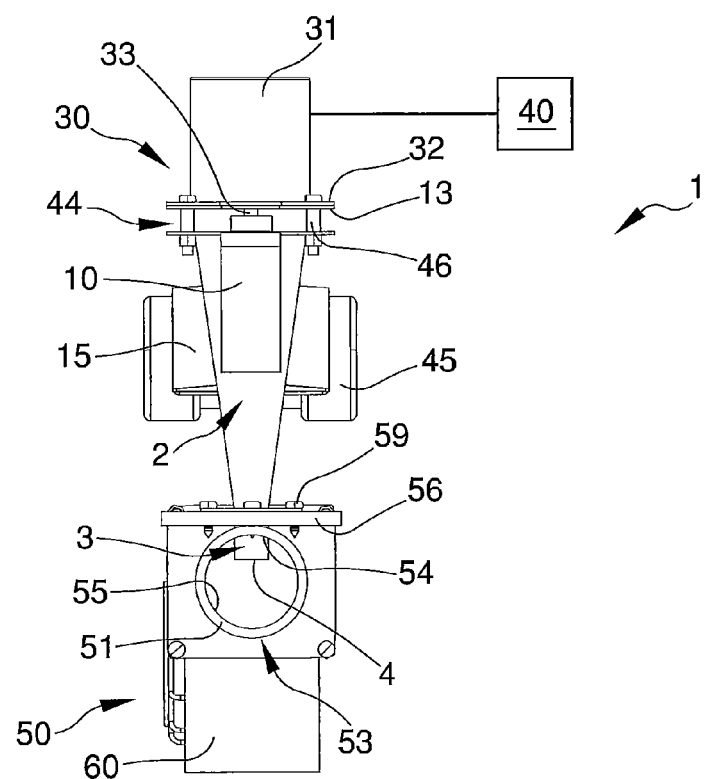
FIG. 3 is a front view of the device of FIG. 2.
Figure 4:
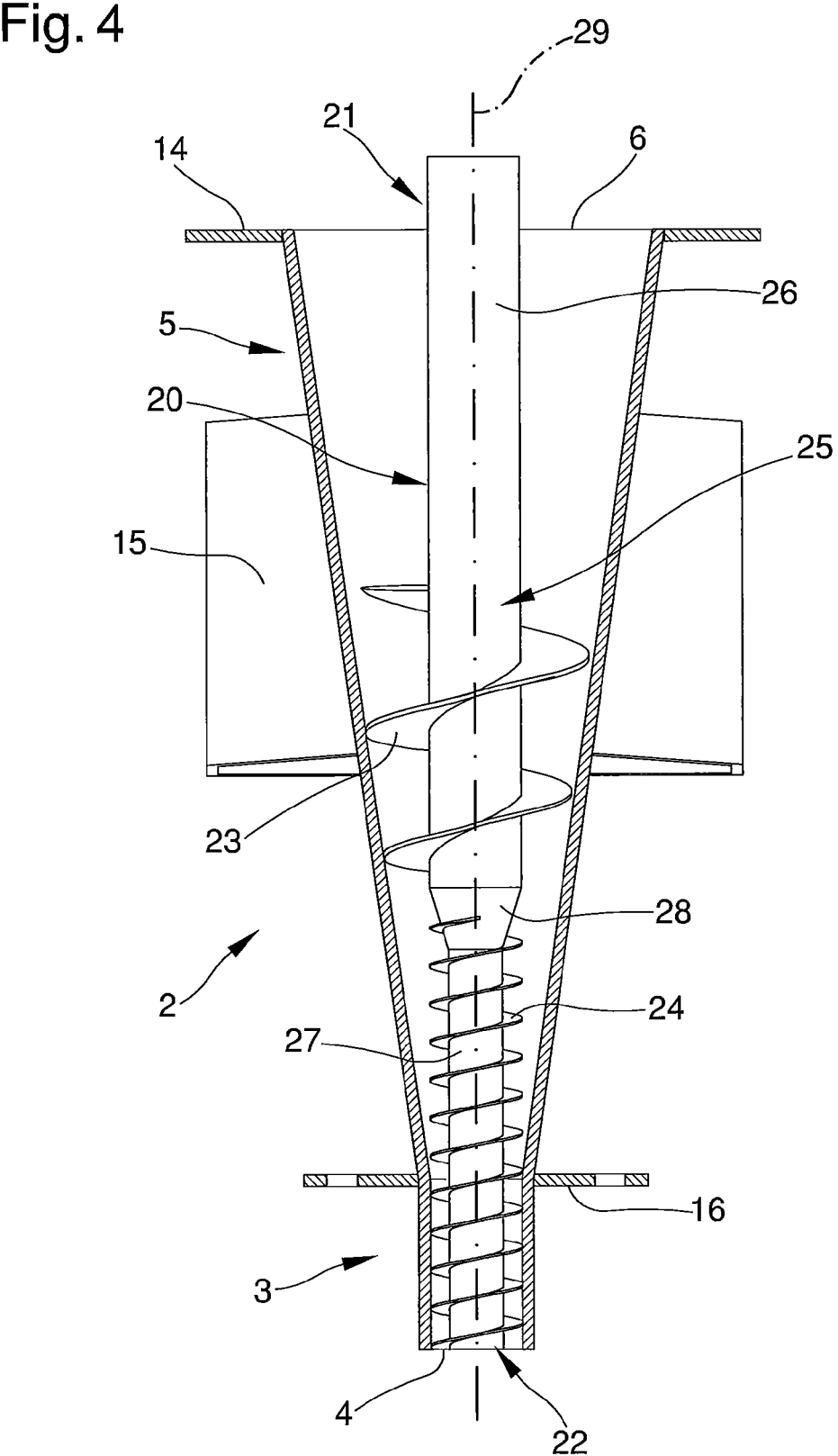
FIG. 4 is a partial sectioned view of the device of FIG. 2 with some parts removed, sectioned along section line IV-IV.

With reference to the accompanying figures, a device for supplying micronized medical salt according to the present invention is globally referred to with the numeral 1.

The device 1 for supplying micronized medical salt comprises a container 2 able to contain a quantity of medical salt, having a vertical longitudinal development and a lower end portion 3 of cylindrical shape and provided with a mouth of release 4 of the medical salt.

The device further comprises a screw 20, inserted into the container 2 and provided with an upper end 21 and a lower end 22 which is free in correspondence of the lower end portion 3, and rotation members 30 of the screw mechanically connected to the upper end of the screw for rotating the latter with respect to the container. The device further comprises a dispenser 50 comprising a supply duct 51 and a ventilation member 60 which generates an air flow within the supply duct. The mouth of release 4 of the medical salt is in communication with the supply duct 51 so as to release the medical salt directly in the aforesaid air flow, and the supply duct is configured so that said air flow is substantially horizontal, at least in correspondence of the mouth of release. Exemplary, as shown in the figures, the supply duct is horizontal (perpendicular to the longitudinal development of the container) so that the air flow generated by the ventilation member is horizontal at every point of the duct itself and escapes from it horizontally.

Preferably, the container 2 has an upper portion 5 of substantially truncated conical shape developing from an upper opening 6, from which the medical salt is introduced in the container, to the aforesaid lower end portion 3. Preferably, said upper opening has a diameter greater than the diameter of the lower end portion of truncated conical shape.

Exemplary, the upper opening 6 has a diameter equal to about 50 mm, the mouth of release 4 of the salt has a diameter equal to about 15 mm, and the distance between the upper opening and the mouth of release of the salt, calculated along the aforesaid vertical longitudinal development of container, is equal to about 150 mm.

Preferably the upper end 21 of the screw comes out superiorly from the upper opening of the container for being connected to the rotation members 30.

Preferably, the upper portion 5 and the lower end portion of the container have a respective axis in common 29 and the screw rotates, with respect to the container, around an axis of rotation coincident with such an axis in common.

Preferably, the screw 20 comprises a first screw 23, having a first pitch and developing, when the device is assembled, entirely within said upper portion 5 of the container, and a second screw 24, having a second pitch and developing lower than the first screw and until the lower end portion 3 of the screw.

Preferably, the first and second screw are arranged in series on the screw (the first screw in upper position with respect to the second) and rotate integrally with it. Preferably, the first pitch is greater than the second pitch. Preferably the second screw partially extends also within the upper portion of the container.

Preferably, the first pitch is greater than 5 mm, preferably 10 mm, and less than 25 mm, preferably 20 mm, and the second pitch is greater than 1 mm, preferably 2 mm, and less than 10 mm, preferably 8 mm. Exemplary first and second pitch are equal to about 18 mm and 5 mm, respectively.

Preferably, the first screw 23 has a truncated conical development substantially corresponding to the truncated conical shape of the upper portion 5 of the container, so that the diameter of each portion of the first screw is substantially equal to the diameter of the corresponding section of the upper portion of the container. Preferably, the diameter of the first screw is between 50 mm and 80 mm, preferably between 25 mm and 40 mm. Preferably, the second screw 24 has a diameter which is constant and substantially equal to the (preferably constant) diameter of the lower end portion 3 of the container and/or of the mouth of release.

Preferably, the first and/or the second screw are medical salt tight with the inner walls of the upper portion and the lower end portion, respectively, of the container.

Preferably the screw comprises a stem 25 having a first portion 26 on which the first screw extends and a second portion 27 on which the second screw extends. Preferably, the first portion of the stem has a respective constant diameter which is greater than a respective constant diameter of the second portion of the stem, the latter having a connecting portion 28 between the first and the second portion. Preferably, the first screw 23 ends inferiorly in correspondence of, or superiorly on, the connecting portion and the second screw begins superiorly in correspondence of, or inferiorly on, the connecting portion 28. Preferably the second screw extends immediately below the first screw, realizing an assembly screw substantially continuous. Preferably, the container comprises a chute 10, for entering the medical salt in the container, which develops externally from a lateral surface of the upper portion of the container until an entry section 11 from which the medical salt is inserted, and the chute is in communication with the interior of the container. Thus the insertion of the micronized medical salt in the container is easy and always possible, without having to disassemble components of the device and also during the operation of the same. Moreover, the use of the chute allows the introduction of the medical salt in the container in agreement with the direction of the slide of the medical salt in the container. Preferably the chute and the container are made in one piece.

Preferably, the chute includes a security grate 12 arranged in correspondence of the entry section 11 of the chute. Thus the chute remains accessible for inserting (before, or during, the operation of the device) the micronized medical salt to be supplied, but inaccessible, for example, for objects having large size (which might be introduced accidentally causing damage to the device) and for the hands of a user. Thus the device is safe and poses no risk to the health of users. Preferably, the device comprises an upper plate 13, which closes the upper opening of the container, provided with a central hole 13a which allows the passage of the upper end 21 of the screw. The upper plate maintains the screw in axis and allows the proper rotation thereof with respect to the container.

Preferably, the container comprises an upper flange 14, which extends horizontally from an upper edge of the upper portion of the container, in correspondence of the upper opening, and forms a ring external to the upper opening; the upper plate 13 is preferably fastened to said upper flange.

Preferably, rotation members 30 comprise a motor 31 provided with a mounting portion 32 superiorly mounted to said container (preferably to the upper plate 13) and with a driving shaft 33 mechanically connected to, and integral with, the upper end of the screw.

Preferably the motor is an electric motor, for example a brushless motor or a DC motor, or a pneumatic or hydraulic actuator. Preferably the drive shaft is mechanically connected to the screw by means of threaded connections (e.g. a dowel) or other fasteners (for example a key, a tongue or a mechanical joint). Preferably, the rotation members may include a speed variator (e.g. a reduction gear), (not shown) interposed between the motor and the screw and able to vary the rotation speed from the motor to the screw, for example to rotate slowly the screw against a high rotation speed of the motor.

Preferably the device comprises an electronic central unit 40, preferably integrated with the motor, programmed for feeding and managing the operation of the rotation members. Preferably the electronic central unit 40 is programmed for allowing a continuous adjustment of the rotation speed of the screw, based on the desired dosage of salt. Thus it is possible to control the dosage of the micronized medical salt supplied by the device.

Preferably the device comprises vibration members 45, stiffly fixed to the container, which vibrates the container himself. Preferably, the container comprises a mounting bracket 15, stiffly and externally fixed to the container (preferably to the upper portion), onto which vibration members are mounted.

Preferably vibration members generate a vibration having a frequency greater than 10 Hz, preferably 50 Hz, and less than 1000 Hz, preferably 500 Hz. Preferably, vibration members include an eccentric mechanical vibrator or a reciprocating motion mechanical vibrator.

Preferably vibration members are connected to the electronic central unit 40 which manages the operation of the vibration members.

Preferably the device comprises a vibration damping system 44 interposed between the container and the rotation members.

Preferably said damping system comprises at least one damper 46 interposed between, and in contact with, the upper plate 13 and the upper flange 14 of the container. In such configuration, the upper plate does not completely occlude the upper opening of the container but it is spaced from it of a distance equal to the axial dimension of said at least one damper. Preferably, the vibration damping system comprises a plurality of dampers 46 (exemplary three) arranged along a circumference centered on the drive shaft 33. These dampers are exemplary cylindrical spacers (provided with a through hole for the mounting to the container and to the motor) made with a material capable to absorb vibrations, for example rubber, plastic or other elastic material. Preferably the device comprises fastening members 35 (e.g. threaded connections, screws, bolts or welds) for mounting the rotation members to the container. Preferably, said fastening members realize at the same time the assembling of the mounting portion 32 of the motor to the upper plate 13 and the assembling of the latter to the upper flange 14 of the container. Preferably, the fastening members 35 also realize the assembling of the dampers 46 interposed between motor and container.

Preferably the supply duct 51 has a horizontal longitudinal development and is provided with an entrance 52, onto which the ventilation member 60 is mounted and from which the air of said air flow enters in the supply duct, and with a free exit 53, opposite to the entrance, from which the air flow and the micronized medical salt come out.

Preferably the supply duct further comprising an operative opening 54 positioned in an intermediate position between said entrance and said exit, and the lower end portion 3 of the container is at least partially introduced into the supply duct through such an operative opening so that the mouth of release is inside the duct at a certain distance from the inner surface 55 of the duct and preferably in a central position with respect to a section which is transversal to the horizontal longitudinal development of the supply duct.

Preferably the supply duct 51 comprises a mounting plate 56, externally fixed (e.g. welded) to an outer surface 57 of the supply duct and provided with a through hole 58 coaxial with the operative opening 54, the mounting plate allowing the passage of the mouth of release of the salt in the through hole until the inside of the supply duct and the rigid fastening of the lower end portion of the container to the supply duct itself.

Preferably the container comprises a lower flange 16 developing, preferably horizontally, from a respective lateral surface of the lower end portion 3. This lower flange is stiffly fixed (e.g. by screws 59) to the mounting plate 56 of the supply duct 51 so that the mouth of release 4 of the salt is within the supply duct at a predetermined distance from the inner surface 55 of the duct itself.

Preferably the ventilation member 60 comprises an electric, centrifugal or axial, fan which generates in the supply duct an air flow that is parallel to the horizontal longitudinal development of the supply duct. Preferably the entrance 52 of the supply duct comprises a mounting flange 61 onto which the fan is mounted, for example by appropriate threaded connections.

Preferably the container and/or the dispenser are made of metal, for example stainless steel, or of plastic, for example polymethylmethacrylate.

The operation of the device initially involves to introduce a mixture of micronized medical salt in the container 2, for example from the upper opening 6 or from the chute 10. Subsequently the rotation of the screw 20, generated by the rotation members 30, advances the mixture in a controlled manner downward along the vertical longitudinal development of the container, until releasing the mixture from the mouth of release 4 of the lower end portion 3 of the container within the supply duct 51. In such duct the ventilation member 60 generates a horizontal air flow, from the entrance 52 to the exit 53, able to supply the mixture, present in the air flow, from the exit of the supply duct to the external environment in which is intended to realize an halotherapy treatment.

Preferably, in operation, the screw rotates at a speed between 1 and 15 rpm, preferably between 4 and 10 rpm. Exemplary, in operation, the dosage of the salt supplied by the device is between 1 and 10 milligrams per hour.

Preferably, the dosage of the salt supplied by the device is adjusted so as to realize, after a certain operating time, a predetermined concentration of micronized medical salt in the environment in which is intended to realize an halotherapy treatment, on the base of the volume of said environment and/or of the possible replacement of the air from outside and/or of the deposit of medical salt on the walls which surround the environment. Exemplary, said concentration is between 1 and 20 milligrams per cubic meter.

Preferably, the mixture is drawn from an envelope containing a mixture of salts having the same chemical composition and different granulometry according to predetermined mass fractions.

For example, said envelope contains a mass percentage of micronized medical salt having a granulometry lower than 20 micrometers, preferably 15, and greater than 5 micrometers, preferably 10, between 50% and 90% and a mass percentage of micronized medical salt having a granulometry lower than 5 micrometers, preferably 3, between 10% and 50%.

Alternatively, said envelope contains a mass percentage of micronized medical salt having a granulometry lower than 30 micrometers, preferably 15, and greater than 5 micrometers, preferably 10, between 5% and 10%, a mass percentage of micronized medical salt having a granulometry lower than 5 micrometers, preferably 3, between 1% and 5% and a mass percentage of micronized medical salt having a granulometry greater than 50 micrometers, preferably 100, between 85% and 94%.

Exemplary, the envelope contains a mass percentage of micronized medical salt having a granulometry lower than 10 micrometers between 5% and 10% and a mass percentage of micronized medical salt having a granulometry greater than 100 micrometers between 90% and 95%.

The invention claimed is:

1. A device (1) for supplying micronized medical salt comprising:
    a container (2) having a vertical longitudinal development and a lower end portion (3) of cylindrical shape and provided with a mouth of release (4) of the medical salt, the container being configured for containing a quantity of medical salt;
    a screw (20) inserted into said container and having an upper end (21) and a lower end (22), the lower end being free in correspondence of said lower end portion;
    rotation members (30) of the screw mechanically connected to the upper end of the screw for rotating the latter with respect to the container,
the screw being configured for advancing said medical salt downward along said longitudinal development through said rotation, so that the medical salt is released in a controlled manner from said mouth of release (4) of the lower end portion (3) and is supported by the screw in any other point on the lower end portion of the container,
the device further comprising a dispenser (50) comprising a supply duct (51) and a ventilation member (60) for generating an air flow within the supply duct, where said mouth of release of the medical salt opens directly into the supply duct so as to release said medical salt directly in the aforesaid air flow and where the supply duct is configured so that said air flow is substantially horizontal at least in correspondence of said mouth of release;
the container (2) having an upper portion (5) of truncated conical shape developing from an upper opening (6), from which the medical salt is introduced in the container, to the aforesaid lower end portion, said upper opening having a diameter greater than the diameter of said lower end portion, where the screw (20) comprises a first screw (23), having a first pitch and developing entirely within said upper portion of the container, and a second screw (24), having a second pitch and developing lower than said first screw and until said lower end portion of the screw, said first and second screw being configured for rotating integrally with said screw and said first pitch being greater than said second pitch;
said first screw (23) having a truncated conical development corresponding to the truncated conical shape of the upper portion of the container, so that the diameter of each portion of the first screw is substantially equal to the diameter of the corresponding section of the upper portion of the container, and where said second screw (24), at least for the portion developing in correspondence of the lower end portion, has a diameter which is constant and substantially equal to the diameter of the cylindrical lower end portion of the container, said first and second screw being medical salt tight with the inner walls of said upper portion (5) and said lower end portion (3), respectively, of the container.

2. The device (1) according to claim 1, wherein said container (2) comprises a chute (10) for entering the medical salt in the container, said chute developing externally from a lateral surface of said upper portion of the container until an entry section (11) from which the medical salt is inserted, said chute being in communication with the interior of the container.

3. The device (1) according to claim 1, wherein said rotation members (30) comprise a motor (31) provided with a mounting portion (32) superiorly mounted to said container and with a driving shaft (33) mechanically connected to, and integral with, the upper end (21) of the screw, the device comprising an electronic central unit (40) programmed for feeding and managing the operation of the rotation members, the electronic central unit being programmed for allowing a continuous adjustment of the rotation speed of the screw.

4. The device (1) according to claim 1, comprising vibration members (45), stiffly fixed to said container and configured for vibrating said container.

5. The device (1) according to claim 4, further comprising a vibration damping system (44) interposed between said container and said rotation members.

6. The device (1) according to claim 1, wherein said supply duct (51) has a horizontal longitudinal development and is provided with an entrance (52), onto which said ventilation member is mounted and from which the air of said air flow enters in the supply duct, and with a free exit (53), opposite to said entrance, from which said air flow and said micronized medical salt come out, the supply duct further comprising an operative opening (54) in an intermediate position between said entrance and said exit, said lower end portion (3) of the container being at least partially introduced into the supply duct through said operative opening so that the mouth of release is inside the duct at a certain distance from the inner surface of the duct.

7. A method for supplying micronized medical salt comprising the following steps:
   introducing a mixture of micronized medical salt in a container (2) of a device (1) according to claim 1;
   advancing said mixture in a controlled manner downward along the vertical longitudinal development of the container, by rotating the screw (20);
   releasing the mixture from the mouth of release (4) of the lower end portion (3) of the container within the supply duct (51);
   generating, by means of the ventilation member (60), an air flow inside the supply duct, the air flow being substantially horizontal at least in correspondence of the mouth of release;
   supplying the mixture, released into the air flow, from the supply duct;
wherein the step of introducing a mixture of micronized medical salt in the container, said mixture is drawn from an envelope containing a mixture of salts having the same chemical composition and different granulometry according to predetermined mass fractions.

8. The method according to claim 7 where, in the step wherein said mixture is drawn from an envelope, said envelope at least contains a mass percentage of micronized medical salt having a granulometry lower than 20 micrometers and greater than 5 micrometers between 5% and 10%, a mass percentage of micronized medical salt having a granulometry lower than 5 micrometers between 1% and 5% and a mass percentage of micronized medical salt having a granulometry greater than 50 micrometers between 85% and 94%.

* * * * *